United States Patent [19]

Abeler et al.

[11] 4,297,268

[45] Oct. 27, 1981

[54] 1,4-DIHYDRO-2,6 DIMETHYLYRIDINE-3,5-DICARBOXYLIC ACID ESTER COMPOSITIONS

[75] Inventors: Gerd Abeler, Griesheim über Darmstadt; Rudolf Maul, Lorsch, both of Fed. Rep. of Germany

[73] Assignee: Ciba-Geigy Corporation, Ardsley, N.Y.

[21] Appl. No.: 105,796

[22] Filed: Dec. 20, 1979

Related U.S. Application Data

[62] Division of Ser. No. 958,760, Nov. 8, 1978, Pat. No. 4,214,088.

[30] Foreign Application Priority Data

Nov. 11, 1977 [CH] Switzerland .................. 13799/77

[51] Int. Cl.$^3$ ................................................. C08K 5/34
[52] U.S. Cl. .......................... 260/45.8 N; 260/45.75 S; 260/23 XA; 260/29.1 R; 252/405
[58] Field of Search .................... 546/321; 260/45.8N, 260/23 XA, 29.1 R, 45.75 S; 252/405

[56] References Cited

U.S. PATENT DOCUMENTS 4,209,439  6/1980  Pigerol et al. ................ 260/23 XA

FOREIGN PATENT DOCUMENTS 1294650  11/1972  United Kingdom .
1443613  7/1976  United Kingdom .

OTHER PUBLICATIONS

H. O. Wirth et al., *Pure and Appl. Chem.*, 49, 627, (1977).
Org. Syntheses, Col. vol. II, 214–216.
J. Uldrikjis et al., *Khim Geterotsikl.*, Soedin, 1975 (9), 1230.
CA 84, 17090m, (1976).

*Primary Examiner*—V. P. Hoke
*Attorney, Agent, or Firm*—Luther A. R. Hall

[57] ABSTRACT

Stabilization of chlorine-containing thermoplasts with 1,4-dihydro-2,6-dimethylpyridine-3,5-dicarboxylic acid esters alone or, in particular, together with a metal-containing stabilizer as synergist.

13 Claims, No Drawings

1,4-DIHYDRO-2,6 DIMETHYLYRIDINE-3,5-DICARBOXYLIC ACID ESTER COMPOSITIONS

This is a divisional of application Ser. No. 958,760, filed on Nov. 8, 1978, now U.S. Pat. No. 4,214,088, issued July 22, 1980.

The present invention relates to new stabilisers, and also to their use on their own or particularly together with synergists, for stabilising chlorine-containing thermoplasts.

It is known that stabilisers can be added to chlorine-containing thermoplasts, for example, polyvinyl chloride, in order to reduce damage and/or discoloration in the substrate caused by exposure to heat.

The known effective thermostabilisers include for example organic metal compounds of magnesium, calcium, strontium, barium, zinc, cadmium, tin, lead and antimony. Also mixtures of some of these compounds are known.

There are however also mentioned in patent literature numerous metal-free thermostabilisers for chlorine-containing thermoplasts. Only a small number of products however satisfy technical requirements and are actually used, or example esters of aminocrotonic acid, diphenylthiourea and α-phenylindole. But these too have unfavourable properties, such as insufficient inherent stability and a tendency to decompose at the processing temperature, and/or high volatility and/or poor compatibility with the substrate, and/or lacking stability to light.

Good stable stabilisers which do not have the above mentioned disadvantages are known however from the German Offenlegungsschrift No. 2,436,007. These are compounds of the formula

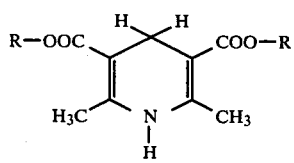

in which R is a hydrocarbon radical, for example an alkyl, cycloalkyl or phenyl group. These stabilisers do indeed induce a good degree of stabilisation over a short period, but are somewhat weaker with regard to long-term stabilisation.

It has now been found that a surprisingly better long-term stabilisation is obtained by using alkoxyalkanol diesters or alkylmercaptoalkanol diesters of 1,4-dihydro-2,6-dimethylpyridine-3,5-dicarboxylic acid.

The subject matter of the present invention is accordingly a stabiliser of the formula (I)

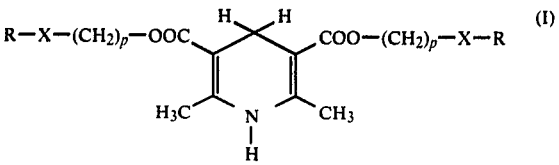

in which R is branched-chain or straight-chain $C_1$-$C_{20}$ alkyl, X is sulfur or oxygen, and p denotes the numbers 1-8 inclusive.

Preferred stabilisers are those of the formula (II)

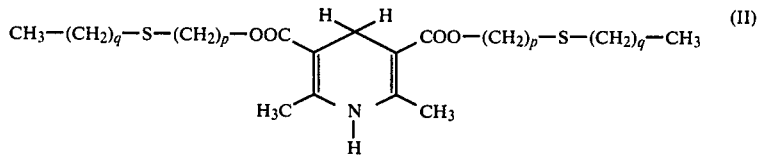

in which p denotes the numbers 1-4 inclusive, particularly 2 and 3, and q denotes the numbers 1-11 inclusive, especially 11.

It has likewise been found that the simultaneous use of a diester of 1,4-dihydro-2,6-dimethylpyridine-3,5-dicarboxylic acid and of a stabiliser containing a metal from the group comprising barium, cadmium, tin or antimony, or also zinc combined with at least one of the aforementioned metals, has a surprisingly strong synergistic effect, that is to say, an effect greater by far than the additive thermostabilising effect to be expected in such a case.

A further subject matter of the present invention is therefore a stabiliser mixture consisting of (a) a dicarboxylic acid diester of the formula (III)

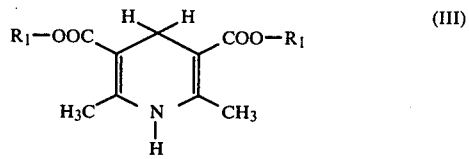

in which $R_1$ is branched-chain or straight-chain $C_1$-$C_{20}$ alkyl, $C_5$-$C_7$ cycloalkyl or phenyl, or a group of the formula $-(CH_2)_p-X-R$ wherein X is sulfur or oxygen, R is branched-chain or straight-chain $C_1$-$C_{20}$ alkyl, and p denotes the numbers 1-8 inclusive; and (b) a stabiliser containing a metal from the group comprising barium, cadmium, tin or antimony, or also zinc combined with at least one of the aforementioned metals.

R and $R_1$ as $C_1$-$C_{20}$ alkyl are straight-chained or branched-chain $C_1$-$C_{12}$ alkyl, especially straight-chain $C_1$-$C_{12}$ alkyl. Examples are: methyl, ethyl, propyl, isopropyl, butyl, tert-butyl, n-pentyl, α-methylpentyl, hexyl, 2,4-dimethylpentyl, octyl, 6-methylheptyl, 2-ethylhexyl, decyl, dodecyl, octadecyl, octadecylethyl and eicosyl. As alkyl, $R_1$ is preferably $C_1$-$C_4$ alkyl, particularly ethyl and also especially dodecyl; and R is preferably dodecyl.

$R_1$ is $C_5$-$C_7$ cycloalkyl is cyclopentyl, cycloheptyl and particularly cyclohexyl.

For the synergistic stabiliser mixture are preferred dicarboxylic acid diesters of the formula (III) in which $R_1$ is a group $-(CH_2)_p-X-R$ having the above-given meaning, and particularly a group —$(CH_2)_p$—S—$(CH_2)_q$—$CH_3$ in which p denotes the numbers 1–4 inclusive, especially 2 and 3, and q denotes the numbers 1–11 inclusive, particularly 11.

Metal-containing stabilisers used are Ba/Cd-, Ba/Zn-, Ba/Cd/Zn- and preferably organotin-stabilisers. They are therefore in particular mixtures of Ba-, Cd- and/or Zn-stearates or -carboxylates, or organotin-mercaptides or -maleates, such as are described for example in Pure and Appl. Chem., Vol. 49, pp. 627–648, Pergamon Press, 1977 (H. O. Wirth, H. Andreas, The Stabilisation of PVC against Heat and Light).

The metal-containing stabilisers to be used according to the invention are generally known, and they are already being used at times for stabilising chlorine-containing thermoplasts.

1,4-Dihydro-2,6-dimethylpyridine-3,5-dicarboxylic acid diesters of the formula (I) are new, and they can be produced both by a new process according to the following equation

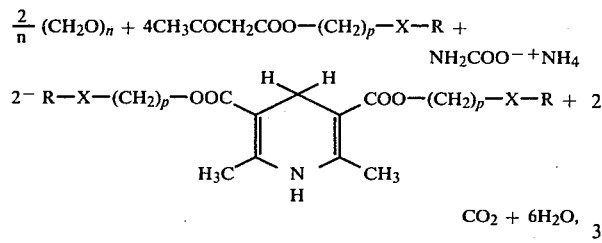

and by processes already known, for example
(a) by the of Hantzsch process (Org. Synth., Coll. Vol. II, pp. 214 and 215), in which acetoacetic ester is reacted with formaldehyde and ammonia; or
(b) by reaction of Urotropin with ammonium acetate (GB Patent Specification No. 1,294,650).

The process (a) is a two-stage process and requires relatively long reaction times, whereas process (b) is similar to the new process mentioned above, both being single-stage processes requiring only short reaction times.

Stabilisers of the formula (III) in which $R_1$ is alkyl, cycloalkyl or phenyl are already known from the German Offenlegungsschrift No. 2,436,007. They can all be produced by any one of the three processes given above.

German Offenlegungsschrift No. 2,436,007 mentions however only stabilisers of the formula (III) in which $R_1$ as alkyl is $C_1$–$C_8$ alkyl. It has however now been found that the stabilisers of the formula (III) in which $R_1$ is dodecyl surprisingly induce an even higher degree of stabilisation.

Further subject matter of the present invention is accordingly the stabiliser 1,4-dihydro-2,6-dimethylpyridine-3,5-dicarboxylic acid-dilauryl ester.

The stabiliser according to the invention, and particularly the synergistic stabiliser mixture according to the invention, are excellently suitable for providing protection against heat-induced degradation of chlorine-containing thermoplasts.

Still further subject matter of the present invention is therefore a stabilised composition comprising a chlorine-containing thermoplastic polymer and, as stabiliser, 0.5–2.5% by weight, preferably 1–2% by weight, of the dicarboxylic acid diester of the formula (I), or preferably a stabiliser mixture of 0.5–2.5% by weight, preferably 1–2% by weight, of the dicarboxylic acid diester of the formula (III) and 0.05–1.5% by weight, preferably 0.2–0.5% by weight, of the metal-containing stabiliser, relative to the total composition.

The individual constituents of the stabiliser mixture are incorporated, either separately or already mixed together, into the thermoplasts, which are to be stabilised, before processing in the customary apparatus.

Chlorine-containing thermoplasts which may be mentioned are: polyvinylidene chloride and preferably polymers formed from or based on vinyl chloride. Preferred are suspension polymers and polymers produced by bulk polymerisation, and also emulsion polymers washed free from emulsifiers. The polyvinyl chloride can be that containing plasticisers or it can be rigid PVC.

Comonomers for thermoplasts based on vinyl chloride which may be mentioned are: vinilidene chloride, transdichloroethane, ethylene, propylene, butylene, maleic acid, acrylic acid, fumaric acid or itaconic acid.

Depending on the purpose for which the moulding compound is to be used, there can be incorporated, before, during or after the addition of the stabiliser or stabiliser mixture according to the invention, further additives, such as lubricants, preferably montan waxes or glycerol esters, fillers, reinforcing fillers such as glass fibres, modifiers such as additives for increasing impact strength, and/or pigments.

Preferred co-additives are light stabilisers, particularly UV stabilisers, which are added generally in amounts of 0.001 to 2% by weight, relative to the total composition. Suitable light stabilisers and UV stabilisers are for example:

2-(2'-Hydroxyphenyl)-benzotriazoles, for example the 5'-methyl-3',5'-di-tert-butyl-, 5'-tert-butyl-, 5'-(1,1,3,3-tetramethylbutyl)-, 5-chloro-3',5'-di-tert-butyl-, 5chloro-3'-tert-butyl-5'-methyl-, 3'-sec-butyl-5'-tert-butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert-amyl-, 3'-methyl-5'-carbomethoxyethyl- and 5chloro-3',5'-di-tert-amyl-derivative.

2,4-Bis-(2'-hydroxyphenyl)-6-alkyl-s-triazines, for example the 6-ethyl-, 6-heptadecyl- or 6-undecyl-derivative.

2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

1,3-Bis-(2'-hydroxybenzoyl)-benzenes, for example 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'-dodecyloxy-benzoyl)-benzene.

Esters of unsubstituted or substituted benzoic acids, for example phenylsalicylates, octylphenylsalicylate, dibenzoylresorcin, bis-(4-tert-butylbenzoyl)-resorcin, benzoylresorcin, 3,5-di-tert-butyl-4-hydroxybenzoic acid-2,4-di-tert-butylphenyl ester or -octadecyl ester or -2-methyl-4,6-di-tert-butylphenyl ester.

Acrylates, for example α-cyano-β,β-diphenylacrylic acid-ethyl ester or -isooctyl ester, α-carbomethoxy-cinnamic acid methyl ester, α-cyano-β-methyl-p-methoxy-cinnamic acid methyl ester or -butyl ester or N-(β-carbomethoxyvinyl)-2-methylindoline.

Nickel compounds, for example nickel complexes of 2,2'-thio-bis-[4-(1,1,3,3-tetramethylbutyl)-phenol], such as the 1:1- or 1:2-complex, optionally with additional ligands such as n-butylamine, triethanolamine or N-cyclohexyl-di-ethanolamine, nickel complexes of bis-[2-hydroxy-4-(1,1,3,3-tetramethylbutyl)-phenyl]-sulfone, such as the 2:1-complex, optionally with additional ligands such as 2-ethylcapronic acid, nickel-dibutyldithiocarbamate, nickel salts of 4-hydroxy-3,5-di-tert-butylbenzyl-phosphonic acid-monoalkyl esters, such as of methyl, ethyl or butyl ester, or nickel complexes of ketoximes, such as of 2-hydroxy-4-methylphenylundecylketonoxime, nickel-3,5-di-tert-butyl-4-hydroxybenzoate or nickel-isopropylxanthogenate.

Sterically hindered amines, for example 4-benzyloxy-2,2,6,6-tetramethylpiperidine, 4-stearoyloxy-2,2,6,6-tetramethylpiperidine, bis-(2,2,6,6-tetramethylpiperidyl)-sebacate or 3-n-octyl-7,7,9,9-tetramethyl-1,3,8-triazaspiro[4,5]decan-2,4-dione.

Oxalic acid diamides, for example 4,4'-di-octyloxyoxanilide, 2,2'-di-octyloxy-5,5'-di-tert-butyl-oxanilide, 2,2-didodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyloxanilide and mixtures thereof with 2-ethoxy-2'-ethyl-5,4'-di-tert-butyl-oxanilide, or mixtures of ortho- and para-methoxy- as well as of o- and p-ethoxy-disubstituted oxanilides.

Compared with the stabilisers described in the German Offenlegungsschrift No. 2,436,007, the stabilisers of the formula (I) according to the invention induce a better longterm stabilisation.

The stabiliser mixture according to the invention ensures an excellent thermostabilising action which exceeds by far that of the individual components.

The following Examples serve to further illustrate the invention. The term 'parts' denotes parts by weight, and percentages are percent by weight.

PRODUCTION EXAMPLES

Example A 1,4-Dihydro-2,6-dimethylpyridine-3,5-dicarboxylic acid-diethyl ester A mixture of
  13.0 g (0.1 mol) of acetoacetic acid ethyl ester,
  4.3 g of formalin (corresponding to 0.05 mol of formaldehyde),
  3.9 g (0.05 mol of ammonium carbaminate,
  85.0 ml of isopropanol, and
  15.0 ml of water,
is heated for 20 minutes at 80° C. After cooling, and concentration by evaporating off the solvent, the 1,4-dihydro-2,6-dimethylpyridine-3,5-dicarboxylic acid-diethyl ester crystallises out.

| yield: | 9.9 g (78% of theory), | | |
|---|---|---|---|
| melting point: | 182–187° C., | | |
| analysis: | % C | % H | % N |
| found: | 61.7 | 7.7 | 5.6 |
| calculated: | 61.6 | 7.6 | 5.5 |

Example B 1,4-Dihydro-2,6-dimethylpyridine-3,5-dicarboxylic acid-di-(2'-ethylthioethyl) ester If the procedure is carried out as in Example A with the single exception that the acetoacetic acid ethyl ester is replaced with 19.0 g (0.1 mol) of acetoacetic acid-(2-ethylthioethyl) ester, there is obtained the 1,4-dihydro-2,6-dimethylpyridine-3,5-dicarboxylic acid-di-(2'-ethylthioethyl) ester.

| yield: | 14.4 g (77% of theory) | | | |
|---|---|---|---|---|
| melting point: | 102–104° C. | | | |
| analysis: | % C | % H | % N | % S |
| found: | 54.3 | 7.1 | 3.6 | 17.1 |
| calculated: | 54.7 | 7.3 | 3.8 | 17.2 |

Example C 1,4-Dihydro-2,6-dimethylpyridine-3,5-dicarboxylic acid-di-(2'-laurylthioethyl) ester If the procedure is carried out as in Example A with the sole exception that the acetoacetic acid-ethyl ester is replaced with 33.1 g (0.1 mol) of acetoacetic acid-(2-laurylthioethyl) ester, there is obtained the 1,4-dihydro-2,6-dimethylpyridine-3,5-dicarboxylic acid-di-(2'-laurylthioethyl) ester.

| yield: | 23.2 g (71% of theory) | | | |
|---|---|---|---|---|
| melting point: | 92–94° C. | | | |
| analysis: | % C | % H | % N | % S |
| found: | 68.2 | 10.6 | 2.1 | 10.0 |
| calculated: | 67.9 | 10.3 | 2.1 | 9.8 |

Example D 1,4-Dihydro-2,6-dimethylpyridine-3,5-dicarboxylic acid-di-(3'-laurylthio-n-propyl) ester If the procedure is carried out as in Example A with the sole exception that the acetoacetic acid ethyl ester is replaced with 20.4 g (0.1 mol) of acetoacetic acid-(3-laurylthio-n-propyl) ester, there is obtained the 1,4-dihydro-2,6-dimethylpyridine-3,5-dicarboxylic acid-di-(3'-laurylthio-n-propyl) ester.

| yield: | 24.2 g (70% of theory) | | | |
|---|---|---|---|---|
| melting point: | 87–90° C. | | | |
| analysis: | % C | % H | % N | % S |
| found: | 68.2 | 10.0 | 2.2 | 9.2 |
| calculated: | 68.7 | 10.5 | 2.1 | 9.4 |

Example E 1,4-Dihydro-2,6-dimethylpyridine-3,5-dicarboxylic acid-di-(2'-ethoxyethyl) ester If the procedure is carried out as in Example A with the sole exception that the acetoacetic acid ethyl ester is replaced with 17.4 g (0.1 mol) of acetoacetic acid-(2-ethoxyethyl) ester, there is obtained the 1,4-dihydro-2,6-dimethylpyridine-3,5-dicarboxylic acid-di-(2'-ethoxyethyl) ester.

| yield: | 12.7 g (68% of theory) | | | |
|---|---|---|---|---|
| melting point: | 97–100° C. | | | |
| analysis: | % C | % H | % N | |
| found: | 59.5 | 8.0 | 4.0 | |
| calculated: | 59.8 | 8.0 | 4.1 | |

APPLICATION EXAMPLES

Testing for thermostability

A dry mixture consisting of 100 parts of S-PVC (K value 58), 4 parts of epoxidised soybean oil, 0.2 part of montan wax, 5 parts of MBS* (modifying agent), 2 parts of PMMA* (processing auxiliary) and the dihydropyridinecarboxylic acid ester and metal-containing stabiliser in the amounts given in the following Table in % (relative to the total composition) is rolled on a roll mill for 5 minutes at 190° C. Test sheet specimens 0.3 mm in thickness are taken from the rolled sheet.

*MBS = methacrylic acid ester/butadiene/styrene copolymer

*PMMA = polymethyl methacrylate

The sheet specimens are exposed to heat in an oven at 180° C., and every 3 minutes the Yellowness Index (YI) according to ASTM D 1925-70 is determined on a specimen.

The results are summarised in the following Table.

| Test No. | Test substances Dihydropyridinedicarboxylic acid ester | %* | Metal-containing stabiliser | %* | Yellowness Index according to ASTM D 1925-70 and exposure to heat (min.) | | | | | | | | | | | | |
|---|---|---|---|---|---|---|---|---|---|---|---|---|---|---|---|---|---|
| | | | | | 3 min. | 6 min. | 9 min. | 12 min. | 15 min. | 18 min. | 21 min. | 24 min. | 27 min. | 30 min. | 33 min. | 36 min. | 39 min. | 42 min. | 45 min. |
| 1 | — | — | — | — | 44 | >100 | | | | | | | | | | | | | |
| 2 | Example A | 1.5 | — | — | 11 | 17 | 33 | 63 | 87 | >100 | | | | | | | | | |
| 3 | Example B | 1.5 | — | — | 14 | 20 | 29 | 46 | 67 | 94 | | | | | | | | | |
| 4 | — | — | BCM* | 0.5 | 12 | 23 | 42 | 87 | >100 | | | | | | | | | | |
| 5 | Example A | 1.5 | BCM | 0.5 | 11 | 11 | 11 | 11 | 13 | 22 | 34 | | >100 | | | | | | |
| 6 | Example B | 1.5 | BCM | 0.5 | 12 | 13 | 13 | 14 | 18 | 23 | 31 | 87 | >100 | | | | | | |
| 7 | — | — | MTS* | 0.2 | 13 | 22 | 44 | 62 | 75 | 95 | >100 | | | | | | | | |
| 8 | Example A | 1.5 | MTS | 0.2 | 12 | 13 | 14 | 16 | 18 | 22 | 27 | 33 | 47 | 59 | 92 | >100 | | | |
| 9 | Example B | 1.5 | MTS | 0.2 | 13 | 16 | 17 | 18 | 19 | 21 | 23 | 24 | 25 | 29 | 32 | 42 | 57 | >100 | |
| 10 | — | — | BTS* | 0.2 | 6 | 10 | 16 | 20 | 29 | 39 | 49 | 62 | 69 | 77 | 88 | 91 | 98 | >100 | |
| 11 | Example A | 1.5 | BTS | 0.2 | 11 | 11 | 11 | 11 | 15 | 17 | 19 | 25 | 31 | 46 | 70 | 88 | >100 | | |
| 12 | Example B | 1.5 | BTS | 0.2 | 12 | 13 | 13 | 15 | 16 | 19 | 21 | 23 | 27 | 29 | 37 | 45 | 66 | 79 | 90 |
| 13 | — | — | DBTM* | 0.2 | 37 | 86 | >100 | | | | | | | | | | | | |
| 14 | Example A | 1.5 | DBTM | 0.2 | 12 | 13 | 17 | 23 | 27 | 34 | 57 | 91 | >100 | | | | | | |
| 15 | Example B | 1.5 | DBTM | 0.2 | 14 | 17 | 20 | 26 | 32 | 42 | 53 | 66 | 87 | >100 | | | | | |
| 16 | Example E | 1.5 | — | — | 19 | 34 | 67 | 100 | | | | | | | | | | | |
| 17 | Example E | 1.5 | MTS | 0.2 | 13 | 13 | 15 | 17 | 21 | 25 | 31 | 36 | 41 | 48 | | | | | |

*% = relative to the total composition
*BCM = pulverulent stabiliser, mixture of Ba- and Cd-myristinate
*BTS = butylthiostannic acid $(C_4H_9SnS_{1.5})_n$
*MTS = monobutyltin stabiliser of the formula
$C_4H_9Sn(SCH_2COO-(CH_2)_4-CH-CH_3)_3$
            $|$
           $C_2H_5$

*DBTM = dibutyltin maleinate 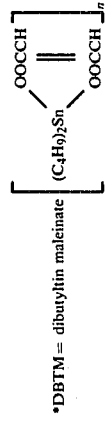

We claim:
1. A stabilized composition which comprises
(a) a chlorine-containing thermoplastic polymer, and
(b) from 0.5 to 2.5 percent by weight, relative to the total composition, of a compound of formula I

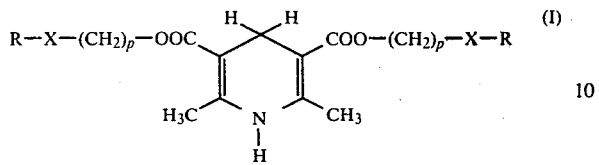

in which R is branched-chain or straight-chain $C_1$–$C_{20}$ alkyl, X is sulfur, and p denotes the numbers 1–8 inclusive.

2. A composition according to claim 1 which additionally contains from 0.05 to 1.5 percent by weight, relative to the total composition, of a metal-containing stabilizer selected from the group consisting of the Ba/Cd carboxylates, Ba/Zn carboxylates, Ba/Cd/Zn carboxylates, organotin mercaptides, organotin maleates and mixtures thereof.

3. A composition according to claim 1 which additionally contains a light stabilizer.

4. A composition according to claim 1 wherein the chlorine-containing thermoplastic polymer is a polymer derived from vinyl chloride.

5. A composition according to claim 4 which also contains a plasticizer.

6. A composition according to claim 4 wherein the polymer is rigid poly(vinyl chloride).

7. A composition according to claim 1 wherein the compound of formula I is

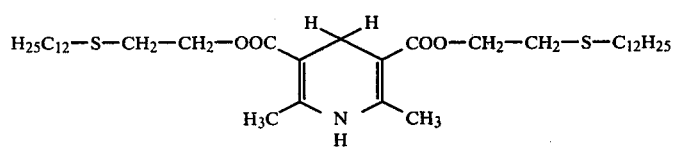

8. A stabilizer mixture consisting of
(a) a compound of formula I

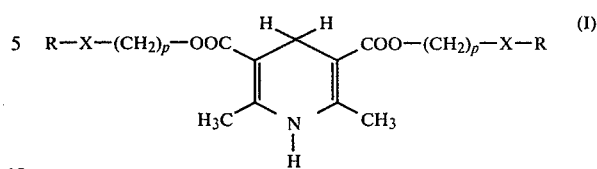

in which R is branched-chain or straight-chain $C_1$–$C_{20}$ alkyl, X is sulphur, and p denotes the numbers 1–8 inclusive, and (b) a metal-containing stabilizer selected from the group consisting of the Ba/Cd carboxylates, Ba/Zn carboxylates, Ba/Cd/Zn carboxylates, organotin mercaptides, organotin maleates and mixtures thereof.

9. A mixture according to claim 8 wherein the compound of formula I is

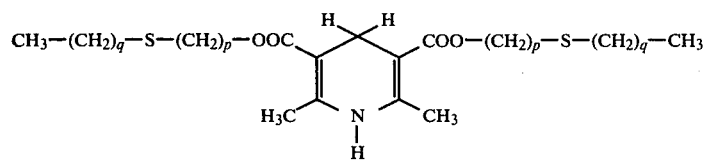

in which p denotes the numbers 1–4 inclusive, and q denotes the numbers 1–11 inclusive.

10. A mixture according to claim 9 where in the compound of formula I p denotes the number 2 or 3, and q denotes the number 11.

11. A mixture according to claim 10 wherein the compound of formula I is

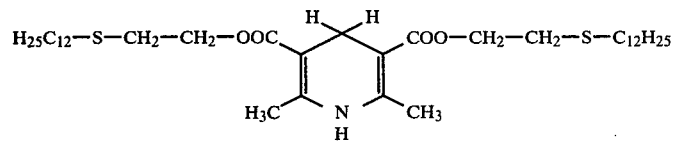

12. A mixture according to claim 8 wherein the metal-containing stabilizer is a Ba/Cd carboxylate, Ba/Zn carboxylate or Ba/Cd/Zn carboxylate.

13. A mixture according to claim 8 wherein the metal-containing stabilizer is an organotin mercaptide or organotin maleate.

* * * * *